United States Patent
Jiang

(10) Patent No.: US 10,584,086 B2
(45) Date of Patent: *Mar. 10, 2020

(54) LIQUID CRYSTAL COMPOUND CONTAINING A DIFLUORMETHOXY BRIDGE AND APPLICATION THEREOF

(71) Applicants: BEIJING BAYI SPACE LCD TECHNOLOGY CO., LTD., Beijing (CN); DONGJIN SEMICHEM CO., LTD., Incheon (KR)

(72) Inventor: Zhanying Jiang, Shaoxing (CN)

(73) Assignees: BEIJING BAYI SPACE LCD TECHNOLOGY CO., LTD, Beijing (CN); Dongjin Semichem Co., Ltd., Seo-gu, Incheon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,215

(22) PCT Filed: Jun. 1, 2015

(86) PCT No.: PCT/CN2015/080516
§ 371 (c)(1),
(2) Date: Oct. 16, 2017

(87) PCT Pub. No.: WO2016/078389
PCT Pub. Date: May 26, 2016

(65) Prior Publication Data
US 2018/0148398 A1   May 31, 2018

(30) Foreign Application Priority Data
Nov. 20, 2014   (CN) .......................... 2014 1 0667565

(51) Int. Cl.
| | |
|---|---|
| *G02F 1/1333* | (2006.01) |
| *C07C 43/225* | (2006.01) |
| *C07C 37/055* | (2006.01) |
| *C07C 41/09* | (2006.01) |
| *C09K 19/30* | (2006.01) |
| C09K 19/04 | (2006.01) |
| *G02F 1/1368* | (2006.01) |

(52) U.S. Cl.
CPC ........ *C07C 43/225* (2013.01); *C07C 37/0555* (2013.01); *C07C 41/09* (2013.01); *C09K 19/3003* (2013.01); C07C 2601/14 (2017.05); C09K 2019/0466 (2013.01); C09K 2019/301 (2013.01); C09K 2019/3004 (2013.01); C09K 2019/3016 (2013.01); *G02F 1/1368* (2013.01)

(58) Field of Classification Search
CPC ........ C09K 19/3003; C09K 2019/0466; C09K 2019/3004; C09K 2019/301; C09K 2019/3016; G02F 1/1333; G02F 1/1368; C07C 43/225; C07C 37/0555; C07C 41/09; C07C 2601/14

USPC .................................................... 252/299.63
See application file for complete search history.

(56) References Cited

U.S. PATENT DOCUMENTS

| | | |
|---|---|---|
| 5,045,229 A | 9/1991 | Bartmann et al. |
| 7,291,367 B2 | 11/2007 | Kirsch et al. |
| 8,197,709 B2 | 6/2012 | Lietzan et al. |
| 8,211,513 B2 | 7/2012 | Jansen et al. |

(Continued)

FOREIGN PATENT DOCUMENTS

| | | |
|---|---|---|
| CN | 1182085 A | 5/1998 |
| CN | 101294079 A | 10/2008 |

(Continued)

OTHER PUBLICATIONS

International Search Report (in English and Japanese) and Written Opinion of the International Searching Authority (in Japanese) issued in PCT/CN2015/080516, dated Aug. 20, 2015; ISA/CN.

(Continued)

*Primary Examiner* — Geraldina Visconti
(74) *Attorney, Agent, or Firm* — Harness, Dickey & Pierce, P.L.C.

(57) ABSTRACT

The present invention relates to a liquid crystal compound having a structure as shown by formula I, wherein R is selected from H and alkyl or alkoxy containing 1-12 carbon atoms in which one or more H are unsubstituted or substituted with halogens; $A_1$, $A_2$ and $A_3$ are each independently selected from: a single bond, 1,4-cyclohexylene, 1,4-phenylene, wherein hydrogen in 1,4-phenylene may be each independently substituted with one or more halogens; and $Z_1$ and $Z_2$ are each independently selected from a single bond or —$(CH_2)_2$—. The compound of the invention has the characteristics of low rotational viscosity, large dielectric anisotropy, good mutual solubility and stability. The driving voltage of a device can be remarkably reduced after the compound is added to a composition. Thus, the compound of the invention has prosperous applications in LCD industry.

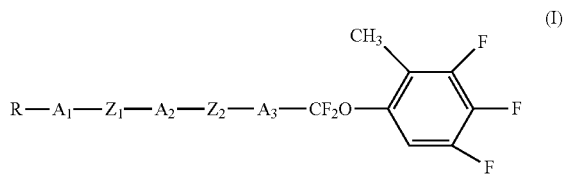

15 Claims, No Drawings

(56) References Cited

U.S. PATENT DOCUMENTS

| | | | |
|---|---|---|---|
| 2006/0061699 A1* | 3/2006 | Kirsch | C09K 19/3402 349/24 |
| 2017/0096601 A1* | 4/2017 | Lee | C09K 19/3003 |
| 2017/0335189 A1* | 11/2017 | Chen | C09K 19/44 |
| 2017/0349830 A1* | 12/2017 | Jiang | G02F 1/1333 |
| 2018/0044592 A1* | 2/2018 | Chen | G02F 1/1333 |

FOREIGN PATENT DOCUMENTS

| | | |
|---|---|---|
| CN | 102050708 A | 5/2011 |
| CN | 102199139 A | 9/2011 |
| CN | 102559202 A | 7/2012 |
| CN | 103937508 A | 7/2014 |
| CN | 104031654 A | 9/2014 |
| CN | 104099105 A | 10/2014 |
| CN | 104449761 A | 3/2015 |
| CN | 104479688 A | 4/2015 |
| CN | 104498053 A | 4/2015 |
| CN | 104498053 B | 5/2016 |
| CN | 104479688 B | 6/2016 |
| JP | 2014210935 A | 11/2014 |
| TW | 201619107 A | 6/2016 |
| TW | 201619357 A | 6/2016 |
| TW | 201619358 A | 6/2016 |
| WO | WO-2014063777 A1 | 5/2014 |
| WO | WO-2016078389 A1 | 5/2016 |
| WO | WO-2016082510 A1 | 6/2016 |
| WO | WO-2016082511 A1 | 6/2016 |

OTHER PUBLICATIONS

International Search Report (in English and Japanese) and Written Opinion of the International Searching Authority (in Japanese) issued in PCT/CN2015/080515, dated Aug. 26, 2015; ISA/CN.

International Search Report (in English and Japanese) and Written Opinion of the International Searching Authority (in Japanese) issued in PCT/CN2015/080517, dated Aug. 26, 2015; ISA/CN.

* cited by examiner

LIQUID CRYSTAL COMPOUND CONTAINING A DIFLUORMETHOXY BRIDGE AND APPLICATION THEREOF

CROSS REFERENCE TO RELATED APPLICATIONS

This application is a U.S. National Phase Application under 35 U.S.C. 371 of International Application No. PCT/CN2015/080516 filed on Jun. 1, 2015 and published in Chinese as WO 2016/078389 on May 26, 2016. This application claims priority to Chinese Patent Application No. 201410667565.5 filed Nov. 20, 2014. The entire disclosures of all of the above applications are incorporated herein by reference.

FIELD OF THE INVENTION

The present invention relates to liquid crystal display materials, particularly to a liquid crystal compound containing a difluoromethoxy bridge and application thereof.

BACKGROUND OF THE INVENTION

Currently, liquid crystal has been applied in information display and some progress has been made in optical communication (S. T. Wu, D. K. Yang. Reflective Liquid Crystal Displays. Wiley, 2001). In recent years, applications of liquid crystal compounds have significantly broadened to various types of display devices, electro-optical devices, electronic components, sensors and the like. For these purposes, a plurality of different structures has been proposed, particularly in nematic phase liquid crystals. Nematic phase liquid crystal compound so far has been widely used in flat panel displays, especially in thin film transistor (TFT) active matrix liquid crystal display (AMLCD) systems.

It has been a long path of development since the discovery of liquid crystals. In 1888, Friedrich Reinitzer, an Austrian botanist, discovered the first liquid crystal material, i.e., cholesteryl benzoate. Manguin invented a rubbing orientation for the production of single domain liquid crystal and initiated the research on optical anisotropy in 1917. E. Bose established Swarm doctrine in 1909, which was supported by experiments of L. S. Ormstein and F. Zernike et al (1918) and later was explained as statistical fluctuations by De Gennes. In 1933, G. W. Oseen and H. Zocher founded continuum theory which was modified by F. C. Frank later in 1958. M. Born (1916) and K. Lichtennecker (1926) found and studied liquid crystal dielectric anisotropy respectively. In 1932, W. Kast accordingly divided the nematic phase into two categories—positive and negative. In 1927, V. Freedericksz and V. Zolinao discovered that nematic liquid crystal would be deformed and presented a voltage threshold (Freederichsz change) in the electric field or magnetic field. The discovery provides a basis for liquid crystal displays.

In 1968, R. Williams in Radio Corporation of America (RCA) found that nematic phase liquid crystals formed domain structure and had light scattering phenomenon in the electric field. G. H. Heilmeir then developed a dynamic scattering mode, the first liquid crystal display in the world. In the early 1970s, Helfrich and Schadt invented twist-nematic (TN) principle. The combination of the TN photoelectric effect and integrated circuit made a display device (TN-LCD), which has opened up a broad prospect for the application of liquid crystals. Since then, due to the development of large scale integrated circuits and the advancement of liquid crystal material, the liquid crystal display, in the art, has made a breakthrough. Super Twist Nematic (STN) mode was proposed successively by T. Scheffer et al. in 1983 through 1985 and an AMLCD mode proposed by P. Brody in 1972 were re-adopted. Conventional TN-LCD technology has been transferred to STN-LCD and TFT-LCD technologies. Although STN scanning lines can be up to 768 lines, there are still some shortcomings such as response speed, viewing angle and gray scale when the temperature rises. Therefore, for a large panel, high information content, high color quality display, an active matrix display becomes the first choice. TFT-LCD has been widely used in direct-view TV, large-screen projection television, computer monitor and certain military instrument display. It is believed that TFT-LCD technologies will have even broader applications.

There are two types of "active matrix" structures: firstly, metal oxide semiconductor (MOS) on a silicon wafer as the substrate. Secondly, thin film transistor (TFT) fabricated on a glass substrate.

Monocrystalline silicon as the substrate has a limitation with its display size due to the fact that there were many problems at junctions of each part of the display unit or module assembly. Accordingly, the second type of TFT active matrix is promising. The photoelectric display effect is generally TFT-TN mode. TFT substrate includes a compound semiconductor, such as of CdSe, a polycrystalline silicon as well as amorphous silicon.

Currently, the TFT-LCD related technologies have been well established and successfully solved technical problems regarding viewing angle, resolution, color saturation and brightness. The display performances of TFT-LCDs are close to or superior to that of CRT displays. Large-screen and small-to-medium-screen TFT-LCD displays have gradually dominated the flat panel displays. However, due to the limitation of the liquid crystal material itself, TFT-LCD still has some defects, such as slow response, high driving voltage, low charge retention rate and so on. Therefore, it is particularly important to search a liquid crystal compound with low viscosity and high dielectric anisotropy.

A liquid crystal structure containing difluoromethoxy bridge bonds is illustrated in U.S. Pat. No. 5,045,229, issued to Merck early in 1989, but an ideal corresponding compound was not obtained.

SUMMARY OF THE INVENTION

With respect to the above-mentioned background, the present invention provides a novel liquid crystal compound having a structure of difluoromethoxy bridge bond unit. The compound is characterized by low rotational viscosity, large dielectric anisotropy, good mutual solubility and stable performance, which has a structure as shown in formula I:

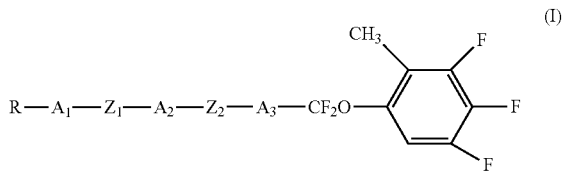

Wherein R is selected from H, and alkyl or alkoxy having 1-12 carbon atoms in which one or more H are unsubstituted or substituted with halogen;

$A_1$, $A_2$ and $A_3$ are each independently selected from: a single bond, 1,4-cyclohexylene, and 1,4-phenylene, wherein hydrogen in 1,4-phenylene may be each independently substituted with one or more halogens; and $Z_1$ and $Z_2$ are each independently selected from a single bond or —$(CH_2)_2$—.

Wherein, in the liquid crystal compound according to the present invention, preferably:

R is selected from H and alkyl or alkoxy containing 1-5 carbon atoms in which one or more H are unsubstituted or substituted with halogen; the halogen is fluorine, chlorine, bromine or iodine, preferably fluorine;

$A_1$, $A_2$ and $A_3$ are each independently selected from: a single bond, 1,4-cyclohexylene, and 1,4-phenylene, wherein hydrogen in 1,4-phenylene may be each independently substituted with one or more halogens; and the halogen is fluorine, chlorine, bromine or iodine, preferably fluorine; and $Z_1$ and $Z_2$ are both single bonds.

In the liquid crystal compound according to the present invention, further preferably:

R is selected from H and unsubstituted alkyl containing 1-5 carbon atoms;

$A_1$ is selected from: a single bond, 1,4-cyclohexylene and 1,4-phenylene, wherein hydrogen in 1,4-phenylene may be each independently substituted with one or more halogens; the halogen is fluorine, chlorine, bromine or iodine, preferably fluorine;

$A_2$ and $A_3$ are each independently selected from: 1,4-cyclohexylene, and 1,4-phenylene, wherein hydrogen in 1,4-phenylene may be each independently substituted with one or more halogens; the halogen is fluorine, chlorine, bromine or iodine, preferably fluorine; and $Z_1$ and $Z_2$ are both single bonds.

And more preferably, the liquid crystal compound is selected from the compounds having structures represented by the following general formulas:

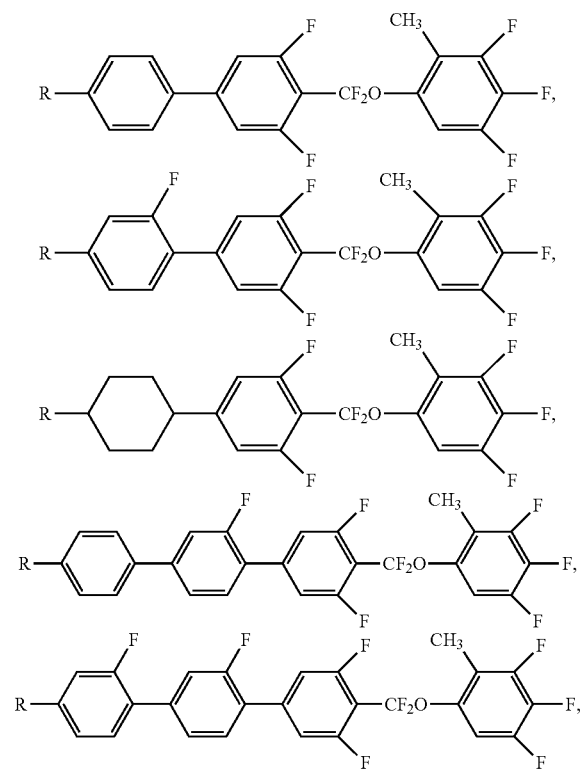

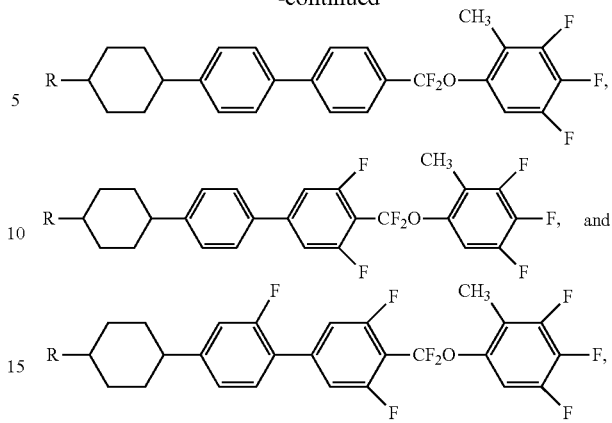

R is selected from alkyl having 1-5 carbon atoms.

As a preferred embodiment of the present invention, the liquid crystal compound is:

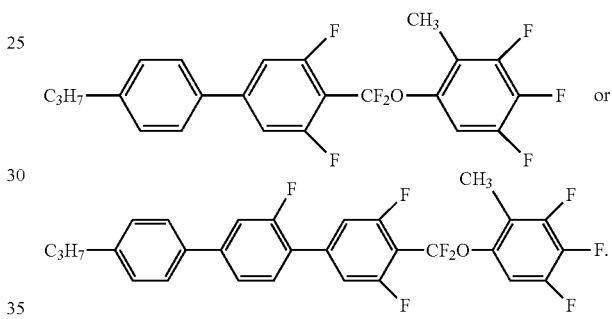

The above compounds have higher dielectric anisotropy, which results in reducing the driving voltage of the device after being applied to a composition.

The second object of the present invention is to provide a method for preparing the above-mentioned liquid crystal compound having difluoromethoxy bridge. The synthetic route of the preparation method is as follows:

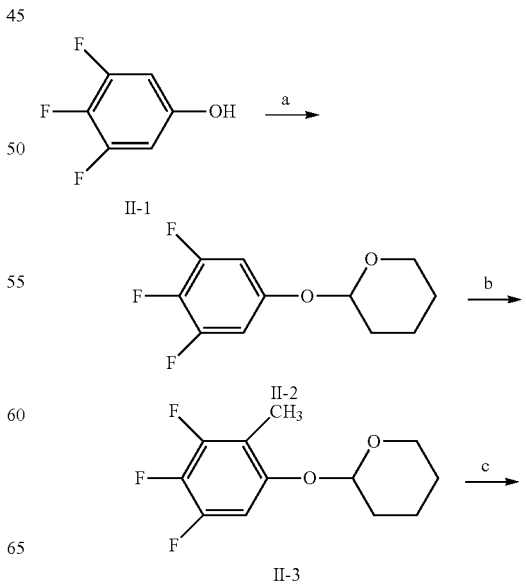

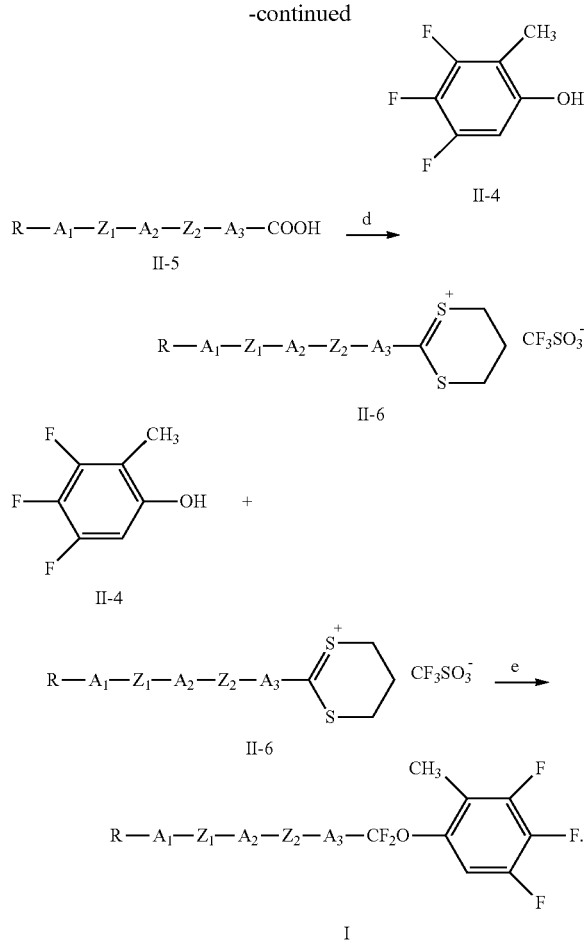

The synthesis comprises the following steps of:

(a) reacting the compound II-1 as a starting material with dihydropyran in the presence of an acid (preferably hydrochloric acid) as a catalyst and dichloromethane as a solvent at room temperature to obtain compound II-2;

(b) reacting the compound II-2 with butyl lithium in the presence of tetrahydrofuran as a solvent at −75° C. to −85° C. under the protection of nitrogen to form a lithium reagent; and then reacting the lithium reagent with methyl iodide to obtain compound II-3;

(c) stirring, heating and reacting the compound II-3 in the presence of pyridinium p-toluenesulfonate as a catalyst to obtain compound II-4;

(d) refluxing and dehydrating the compound II-5 and 1,3-propanedithiol in the presence of trifluoromethyl-sulfonic acid as a catalyst and filtering to obtain compound 11-6; and (e) reacting the compound II-4 with the compound II-6 in the presence of hydrogen fluoride triethylamine as a dehydrating agent and bromine as a catalyst to obtain target compound I;

wherein R, $A_1$, $A_2$, $A_3$, $Z_1$ and $Z_2$ are defined as above.

The liquid crystal compound having difluoromethoxy bridge bonds can be obtained stably in batches by using the above-mentioned preparation method and has the advantages of large dielectric anisotropy, good mutual solubility and stability.

Furthermore, the invention also claims a liquid crystal composition containing the liquid crystal compound having difluoromethoxy bridge, wherein the liquid crystal compound having difluoromethoxy bridge is added in an appropriate approach and the addition amount of 1-80% is preferable, and more preferably is 3-50%. It can be expected for a person skilled in the art that the dielectric anisotropy of the existing conventional liquid crystal composition can be further improved based on the addition of the above-mentioned liquid crystal compound, whereby the driving voltage of the liquid crystal display can be substantially reduced.

A further object of the present invention is to provide the liquid crystal compound having difluoromethoxy bridge bonds and the composition thereof for the state of art liquid crystal displays.

Specifically, the present invention provides the above-mentioned compound or composition for liquid crystal display device. The liquid crystal display device may comprise, but not limited to, TN, ADS, FFS or IPS liquid crystal displays. The liquid crystal display device has the advantage of much lower driving voltage due to the addition of the liquid crystal composition.

Abbreviations of performance testing parameters in the present invention are described as follows:

$\Delta\varepsilon$ represents dielectric anisotropy at 25° C. and 1 kHz;

$\gamma$ 1 represents rotational viscosity (mPa·s) at 25° C.;

$\Delta$ n is optical anisotropy, $n_o$ is refractive index (589 nm, 25° C.);

C.p is clearing point of the liquid crystal composition (° C.);

VHR is voltage holding ratio (%), which is obtained by injecting a mixed liquid crystal into a liquid crystal cell and placing the liquid crystal cell into an incubator, performing the test program after the temperature being stable and manually taking points. The measurement voltage is 5V, the power-on time is 5 ms and the holding time is 500 ms.

DETAILED DESCRIPTION

Example 1

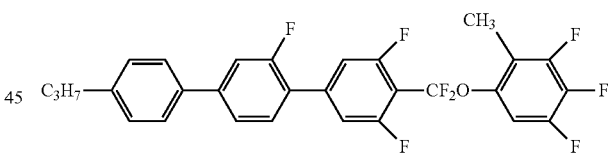

Synthesis of 4-[(3,4,5-trifluoro-2-methyl-phenoxy)-difluoromethyl]-3,5,2'-trifluoro-4"-propyl-[1,1'; 4',1"]terphenyl (Compound 7)

1) Synthesis of 2-(3,4,5-trifluoro-phenoxy)-tetrahydropyran (Compound 2)

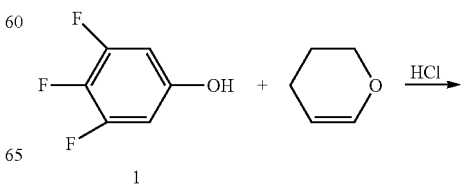

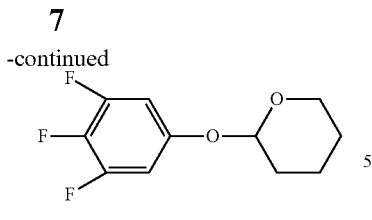

70 g 3,4,5-trifluorophenol, 72 g 2,3-dihydropyran and 140 ml dichloromethane were added into a 500 ml dried and clean three-necked flask, stirred, added dropwise with 5 drops of concentrated hydrochloric acid slowly at room temperature, and reacted for 3 hours after the completion of the dropwise addition. The reaction solution was washed twice with 100 ml 10% aqueous sodium hydroxide solution, dried with 20 g anhydrous sodium sulfate for 30 minutes and subjected to suction filtration, and the filtrate is spin-dried for later use.

2) Synthesis of 2-(3,4,5-trifluoro-2-methyl-phenoxy)-tetrahydropyran (Compound 3)

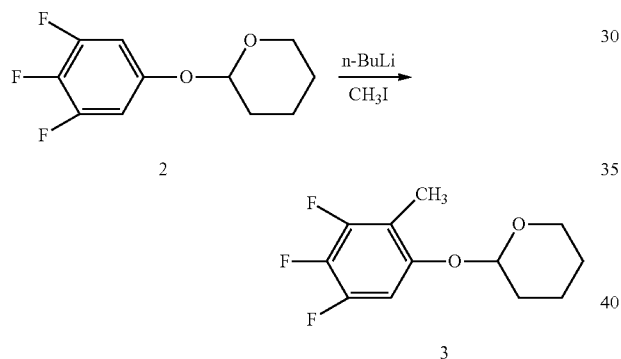

97 g 2-(3,4,5-trifluoro-phenoxy)-tetrahydropyran (Compound 2) and 500 ml tetrahydrofuran were added into a 1 L dried and clean three-necked flask, protected under nitrogen, cooled to −75° C. to −85° C. by using liquid nitrogen, added dropwise with 200 ml butyllithium, reacted for 1 hour under a control of temperature after the completion of dropwise addition, added dropwise with 89 g methyl iodide, reacted for 30 minutes at a temperature controlled at −75° C. to −85° C. after the completion of dropwise addition, and then the temperature was naturally raised to −20° C., the reaction solution was hydrolyzed and destroyed with an aqueous ammonium chloride solution. Liquid separation was performed, the aqueous phase was extracted twice with 100 ml ethyl acetate, the organic phases were combined, washed twice with 100 ml aqueous sodium chloride solution, dried with 30 g anhydrous sodium sulfate for 30 minutes and subjected to suction filtration, and the filtrate is spin-dried and crystallized with 1.5 times of ethanol to obtain a white solid.

Theoretical production: 102 g, actual production: 64 g, yield: 62.7%, white solid, GC: 99.6%, melting point: 67.65° C.

3) Synthesis of 3,4,5-trifluoro-2-methyl-phenol (Compound 4)

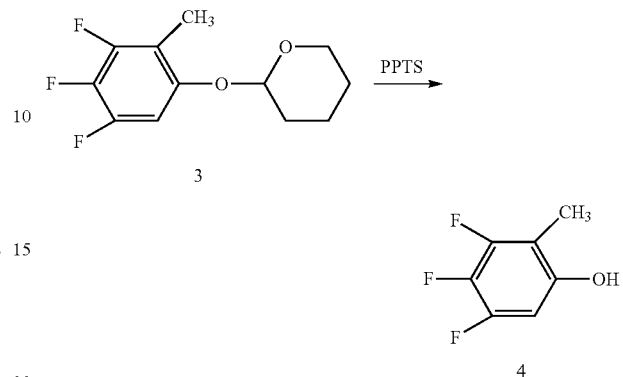

10 g 2-(3,4,5-trifluoro-2-methyl-phenoxy)-tetrahydropyran (Compound 3), 2 g of pyridinium p-toluenesulfonate and 50 ml of ethanol were added into a 100 ml dried and clean three-necked flask, stirred and heated to 60° C.-70° C., and reacted for 3 hours in a timing manner. The reaction solution was spin-dried, added with 20 ml dichloromethane to dissolve the product, washed twice with 10 ml aqueous sodium chloride solution and dried with 10 g anhydrous sodium sulfate for several minutes and spin-dried.

Theoretical production: 6.5 g, actual production: 6.5 g, yield: 100% (according to the theoretical basis), a colorless liquid, GC: 99.155%.

4) Synthesis of onium trifluoromethyl sulfonate (Compound 6)

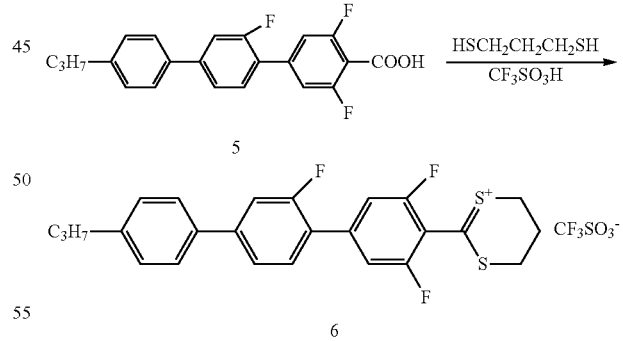

137 g 3,5,2'-trifluoro-4''-propyl-[1,1'; 4',1''] terphenyl-4-carboxylic acid (Compound 5), 47 mL 1,3-propanedithiol, 42 mL trifluoromethyl sulfonic acid, 145 mL toluene and 145 mL isooctane were added into a 1 L three-necked flask, a water separator was mounted at one side opening, the temperature was raised until the refluxing was generated, the reaction was conducted for 6 hours, slowly cooled to 0° C. and subjected to suction-filtration to obtain a solid. The solid was dried for further feeding.

5) Synthesis of 4-[(3,4,5-trifluoro-2-methyl-phenoxy)-difluoromethyl]-3,5,2'-trifluoro-4''-propyl-[1,1'; 4',1'']terphenyl (Compound 7)

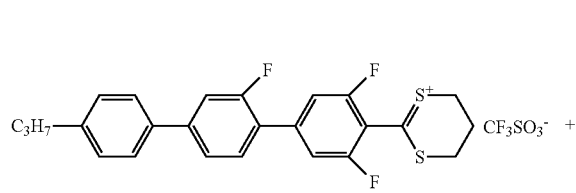

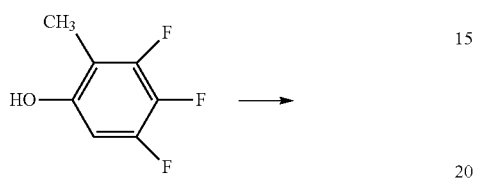

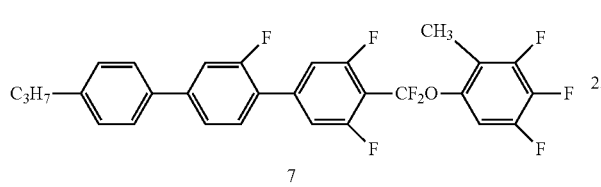

7

200 mL dichloromethane, 39 mL triethylamine and 45.4 g 3,4,5-trifluoro-2-methyl-phenol (Compound 4) were added into a 2 L three-necked flask and cooled to 20° C., added with a solution composed of 142 g onium triflorom-ethyl sulfonate (Compound 6) and 400 mL dichloromethane and stirred for 1 hour. The temperature is controlled below −75° C., 77 g hydrogen fluoride triethylamine was added dropwise and the stirring was continued for 1 hour. The temperature is controlled below −75° C., a solution composed of 15 mL bromine and 30 mL dichloromethane was re-warmed to −10° C. and was subjected to post-processing. 1 L water was added into a 10 L bucket, the stirring was started, the reaction solution was poured and stirred for several minutes, the sodium bicarbonate solid was added slowly (a large amount of gas was generated) until the pH of the solution was nearly neutral, standing for liquid separation, the aqueous phase was extracted once with 500 ml dichloromethane, the organic phases were combined, and the solvent was spin-dried at 70° C. to obtain a solid, recrystallization was carried out with 2-fold ethanol and one-fold toluene for three times and the suction-filtration and air-drying were performed to obtain a white solid. Theoretical production: 128.6 g, actual production: 103 g, yield: 80.0%.

Gas chromatographic (GC) purity is 99.9%,

Melting point: 70.9° C.,

Δn is 0.197,

Δε is 31.5, and

γ1 is 208 mPa·s.

Mass spectrometry fragment: 173,346,375,536 (molecular ion peak);

H-NMR spectrum (CDCl3,300 MHz): δH: 0.90-2.60 (m, 10H), 6.10-7.60 (m, 10H).

Example 2

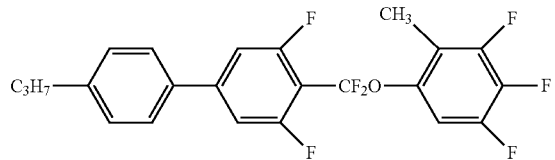

Synthesis of 4-[(3,4,5-trifluoro-2-methyl-phenoxy)-]-difluoro methyl-3,5-difluoro-4'-propyl biphenyl (Compound 10)

1) Synthesis of onium trifluoromethyl sulfonate (Compound 9)

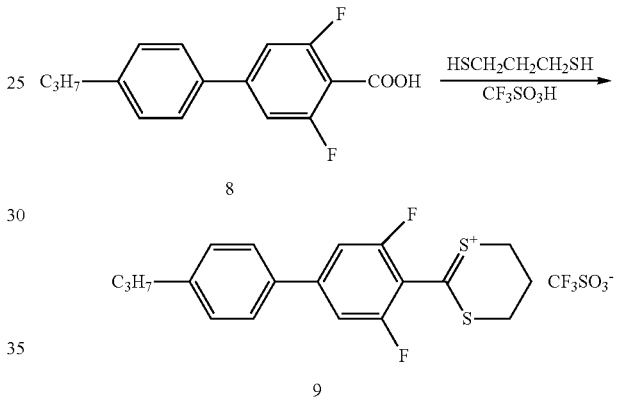

102 g 4'-propyl-3,5-difluorodiphenyl carboxylic acid (compound 8), 47 mL 1,3-propanedithiol, 42 mL trifluoromethyl sulfonic acid, 145 mL toluene and 145 mL isooctane were added into a 1 L three-necked flask, a water separator was mounted at one side opening, the temperature was raised until the refluxing was generated, the reaction was conducted for 6 hours, slowly cooled to 0° C. and was subjected to suction-filtration to obtain a solid, the solid was dried for further feeding.

2) Synthesis of 4-[(3,4,5-trifluoro-2-methyl-phenoxy)-]-difluoromethyl-3,5-difluoro-4'-propyl biphenyl (Compound 10)

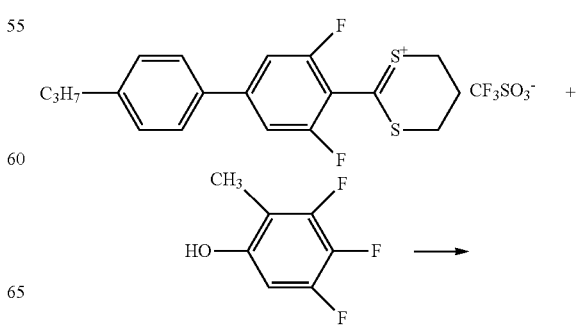

-continued

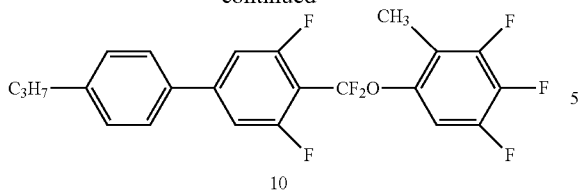

200 mL dichloromethane, 39 mL triethylamine and 45.4 g 3,5-difluoro-4-(3-fluoro-propoxy)-phenol (Compound 4) were added into a 2 L three-necked flask, cooled to 20° C., added with a solution composed of 117 g onium trifluoromethyl sulfonate (Compound 10) and 200 mL dichloromethane and stirred for 1 hour. The temperature was controlled below −75° C., 77 g hydrogen fluoride triethylamine was dropwise added and the stirring was continued for 1 hour. The temperature was controlled below −75° C., a solution composed of 15 mL bromine and 30 mL dichloromethane was re-warmed to −10° C. and subjected to post-processing. 1 L water was added into a 10 L bucket, the stirring was started, the reaction solution was poured and stirred for several minutes, the sodium bicarbonate solid was added slowly (a large amount of gas was generated) until the pH of the solution was nearly neutral, standing for liquid separation, the aqueous phase was extracted once with 500 ml dichloromethane, the organic phases were combined, and the solvent was spin-dried at 70° C. to obtain a sticky substance, recrystallization was carried out with 2-fold ethanol and 0.5-fold petroleum ether for three times and the suction-filtration and air-drying were performed to obtain a white solid. Theoretical production: 106 g, actual production: 69 g, yield: 65.1%.

Gas chromatographic (GC) purity is 99.9%,
Δ n is 0.133,
Δε is 23.0, and
γ 1 is 52.1 mPa·s.
Mass spectrometry fragment: 252, 281, 442 (molecular ion peak);
H-NMR spectrum (CDCl3, 300 MHz): δH: 0.90-2.60 (m, 10H), 6.10-7.50 (m, 7H).

Example 3

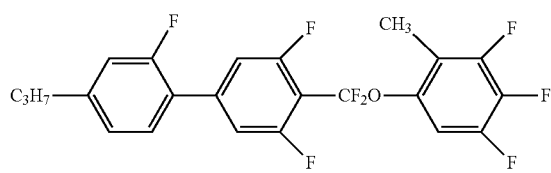

Synthesis of 4-[(3,4,5-trifluoro-2-methyl-phenoxy)-]-difluoromethyl-2',3,5-trifluoro-4'-propyl biphenyl (Compound 13)

1) Synthesis of onium trifluoromethyl sulfonate (Compound 11)

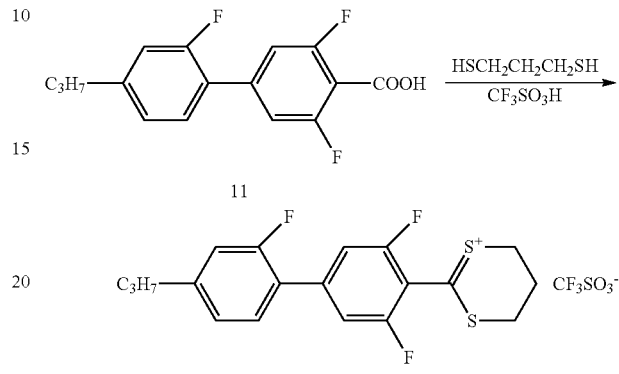

65 g 4'-propyl-2',3,5-trifluorodiphenyl carboxylic acid (compound II), 28 mL 1,3-propanedithiol, 25 mL trifluoromethyl sulfonic acid, 90 mL toluene and 90 mL isooctane were added into a 1 L three-necked flask, a water separator was mounted at one side opening, the temperature was raised until the refluxing was generated, the reaction was conducted for 6 hours, slowly cooled to 0° C. and was subjected to suction-filtration to obtain a solid, the solid was dried for further feeding.

2) Synthesis of 4-[(3,4,5-trifluoro-2-methyl-phenoxy)-]-difluoromethyl-3,5-difluoro-4'-propyl biphenyl (Compound 10)

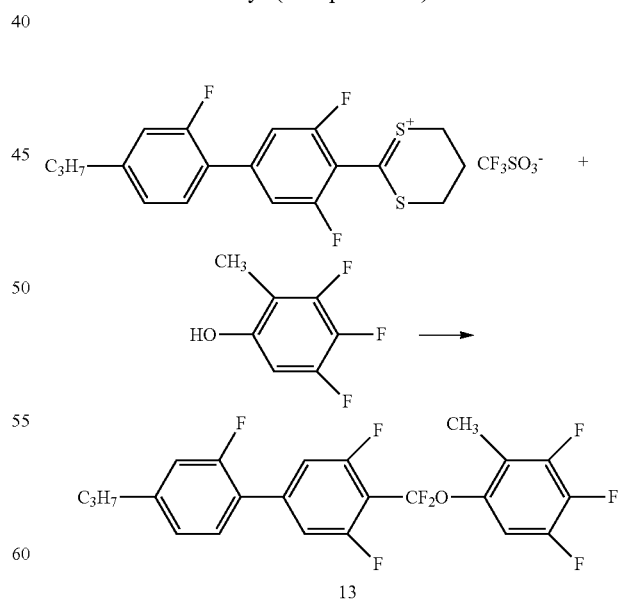

100 mL dichloromethane, 20 mL triethylamine and 23 g 3,5-difluoro-4-(3-fluoropropoxy)-phenol (Compound 4) were added into a 2 L three-necked flask, cooled to 20° C., added with a solution composed of 60.6 g onium trifluoromethyl sulfonate (compound II) and 100 mL dichloromethane and stirred for 1 hour. The temperature was controlled below −75° C., 38 g hydrogen fluoride triethylamine was added dropwise and the stirring was continued for 1 hour. The temperature was controlled below −75° C., a solution composed of 8 mL bromine and 15 mL dichloromethane was re-warmed to −10° C. and subjected to post-processing. 0.5 L water was added into a 5 L bucket, the stirring was started, the reaction solution was poured and stirred for several minutes, the sodium bicarbonate solid was added slowly (a large amount of gas was generated) until the pH of the solution was nearly neutral, standing for liquid separation, the aqueous phase was extracted once with 250 ml dichloromethane, the organic phases were combined, and the solvent was spin-dried at 70° C. to obtain a sticky substance, recrystallization was carried out with 2-fold ethanol and 0.5-fold petroleum ether for three times and the suction-filtration and air-drying were performed to obtain a white solid. Theoretical production: 60.6 g, actual production: 38.3 g, yield: 63%.

Gas chromatographic (GC) purity is 99.9%,
Δn is 0.125,
Δε is 26.5, and
γ1 is 59.8 mPa·s.
Mass spectrometry fragment: 270,299,460 (molecular ion peak);
H-NMR spectrum (CDCl3, 300 MHz): δH: 0.90-2.60 (m, 10H), 6.10-7.50 (m, 6H).

Examples 4-17

According to technical solutions of Examples 1-3, the following compounds can be synthesized by simply replacing starting materials containing the corresponding groups (without substantively adjusting the specific preparation methods):

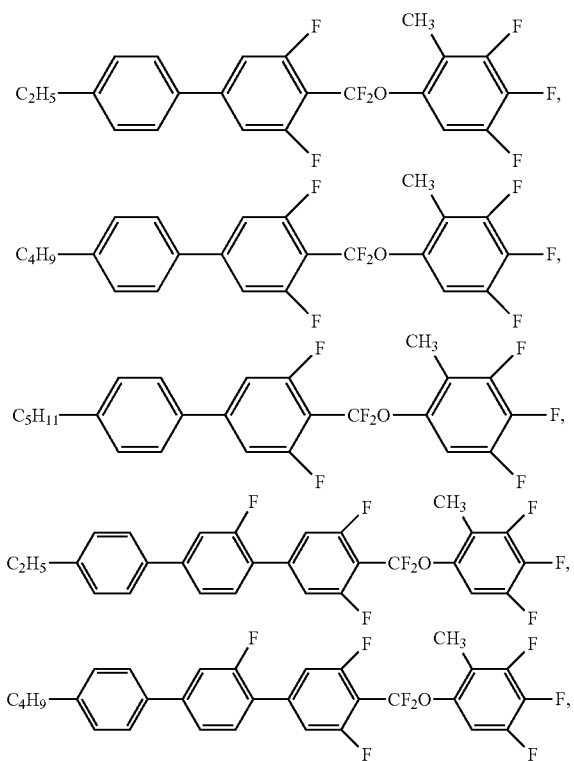

Example 18 Mixed Crystal Composition

Liquid crystal monomers used in the following composition are all provided by BEIJING BAYI SPACE LCD TECHNOLOGY CO., LTD. Unless otherwise specified, the content of each component in the examples is expressed as a mass percentage.

Liquid crystal compounds having the following parts by weight were taken and used for preparing a liquid crystal composition. The specific ratio and performance parameters of the resulting liquid crystal composition are shown in the following table.

The liquid crystal compound having difluoromethoxy bridge has been successfully applied in TN, IPS, FFS, ADS-TFT modes, the results are shown in Tables 1-3.

TABLE 1
Parts by weight of each component and performance parameters of the liquid crystal composition
| Components | Parts | Performance Parameters | |
|---|---|---|---|
| 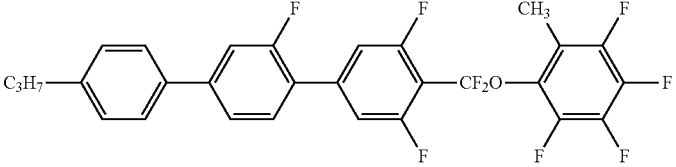<br>(Compound 7) | 10 | Δ n | 0.101 |
| 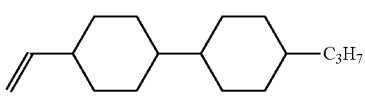 | 22.5 | Δε | 8.21 |
| 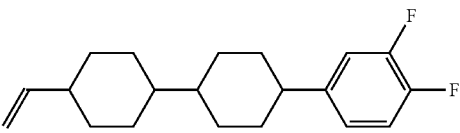 | 22.5 | γ 1 | 86.1 |
| 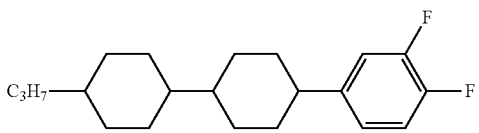 | 18 | C.p (° C.) | 81.5 |
| 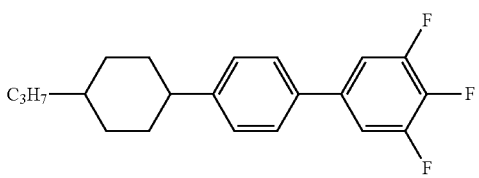 | 13.5 | VHR (%) | 99.5 |
| 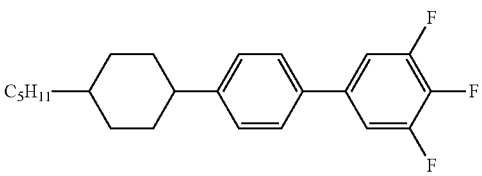 | 13.5 | | |
TABLE 2
Parts by weight of each component and performance parameters of the liquid crystal composition
| Components | Parts | Performance Parameters | |
|---|---|---|---|
| 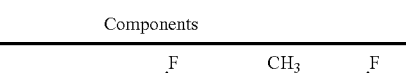<br>(Compound 10) | 10 | Δ n | 0.093 |
| 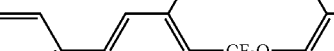 | 22.5 | Δε | 7.37 |

TABLE 2-continued
Parts by weight of each component and performance parameters of the liquid crystal composition
| Components | Parts | Performance | Parameters |
|---|---|---|---|
| 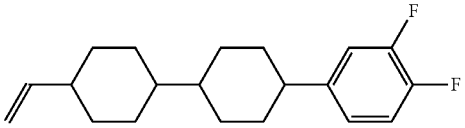 [SMILES: C=CC1CCC(C2CCC(c3ccc(F)c(F)c3)CC2)CC1] | 22.5 | γ 1 | 70.5 |
| 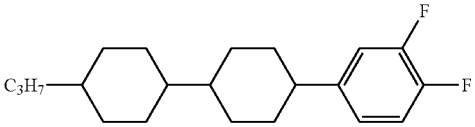 | 18 | C.p (° C.) | 70.2 |
| 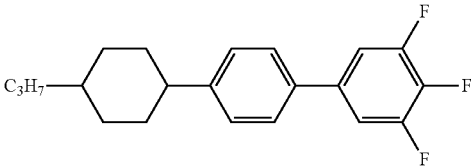 | 13.5 | VHR (%) | 99.5 |
| 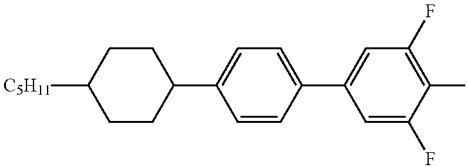 | 13.5 | | |
TABLE 3
Performance parameters of the liquid crystal composition containing the liquid crystal compounds
| Components | Parts | Performance | Parameters |
|---|---|---|---|
| 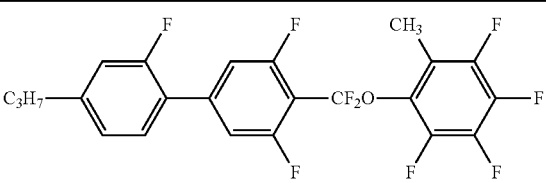<br>(Compound 13) | 10 | Δ n | 0.091 |
| 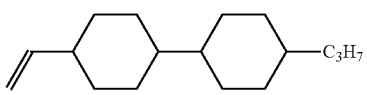 | 22.5 | Δε | 7.72 |
| 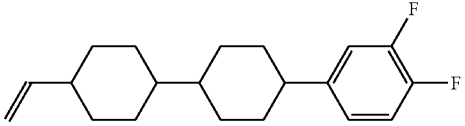 | 22.5 | γ 1 | 71.23 |
| 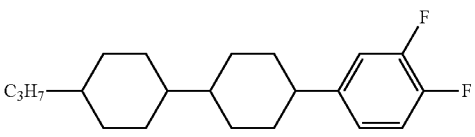 | 18 | C.p (° C.) | 68.7 |

TABLE 3-continued
Performance parameters of the liquid crystal composition containing the liquid crystal compounds
| Components | Parts | Performance Parameters | |
|---|---|---|---|
| 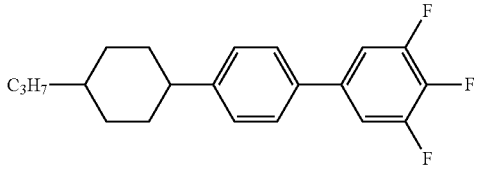 | 13.5 | VHR (%) | 99.5 |
| 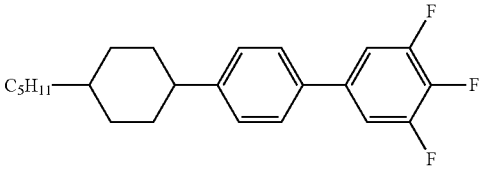 | 13.5 | | |
TABLE 4
Performance parameters of the liquid crystal composition without the addition of the compound of the invention
| Components | Parts | Performance Parameters | |
|---|---|---|---|
| 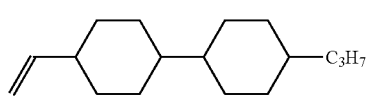 | 25 | Δ n | 0.090 |
| 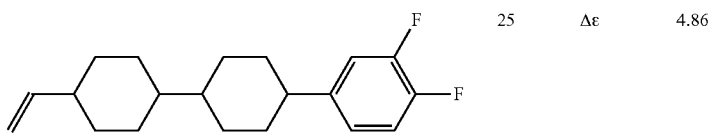 | 25 | Δε | 4.86 |
| 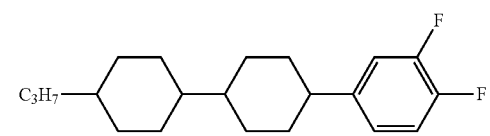 | 20 | γ 1 | 83.4 |
| 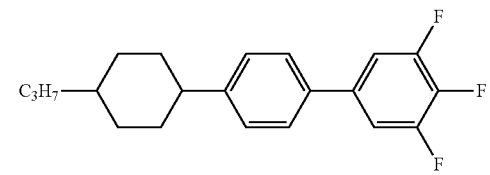 | 15 | C.p (° C.) | 79.1 |
| 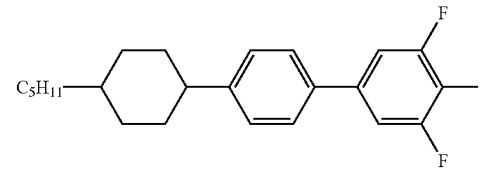 | 15 | VHR (%) | 99.5 |

TABLE 5

Parts by weight of each component and performance parameters of the liquid crystal composition

| Components | Parts | Performance Parameters | |
|---|---|---|---|
| 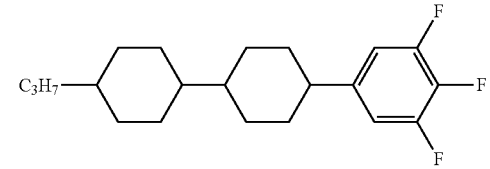 | 10 | Δn | 0.095 |
| 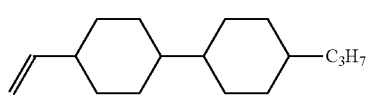 | 22.5 | Δε | 6.05 |
| 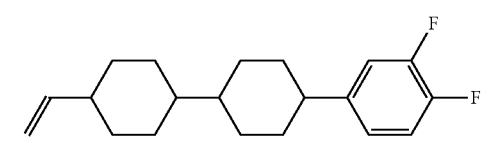 [SMILES: C=CC1CCC(C2CCC(c3ccc(F)c(F)c3)CC2)CC1] | 22.5 | γ1 | 82.1 |
| 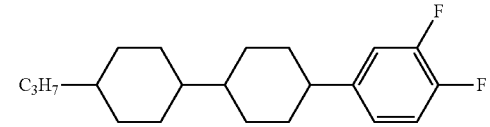 | 18 | C.p (° C.) | 80.5 |
| 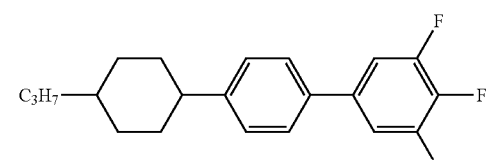 | 13.5 | VHR (%) | 99.5 |
| 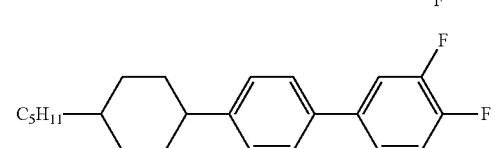 | 13.5 | | |

It can be seen from Tables 1-5 above, that a liquid crystal composition, wherein either the compound of the invention is directly added or the traditional dielectric anisotropy compound (Compound 14) is replaced by the compound of the invention, is moderate in both rotational viscosity and Δn value and high in voltage holding ratio, in particular, is of very high dielectric anisotropy. Meanwhile, in the liquid crystal composition of the present invention, the adding percentage of the compound is in the range of 1-80% and more preferably, in the range of 3-50%.

In addition to the compositions exemplified in the experimental examples, other liquid crystal compositions consisted of other liquid crystal compounds having difluoromethoxy bridge structure introduced in the current invention can also achieve an excellent electro-optical performance.

Although the present invention has been described in detail with general explanation, specific embodiments and experiments, it is obvious to a person skilled in the art that a variety of modifications or improvements can be made based on the present invention. Therefore, all these modifications and improvements made without departing from the scope of the present invention belong to the scope claimed in the invention.

What is claimed is:

1. A liquid crystal compound comprising a difluoromethoxy bridge structure as shown by formula (I):

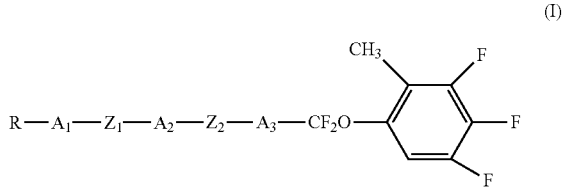

wherein R is selected from H, and alkyl or alkoxy containing 1-12 carbon atoms, wherein one or more H in alkyl or alkoxy are unsubstituted or substituted with halogens;

$A_1$, $A_2$ and $A_3$ are each independently selected from: a single bond, 1,4-cyclohexylene and 1,4-phenylene, when $A_1$, $A_2$, $A_3$ denote 1,4-phenylene, wherein hydrogen in $A_1$, $A_2$, $A_3$ may be each independently substituted with one or more halogens; and $Z_1$ and $Z_2$ are each independently selected from a single bond or $-(CH_2)_2-$.

2. The liquid crystal compound according to claim 1, wherein the compound is characterized in that R is selected from H and alkyl or alkoxy containing 1-5 carbon atoms in which one or more H are unsubstituted or substituted with halogens; the halogen is fluorine, chlorine, bromine or iodine;

$A_1$, $A_2$ and $A_3$ are each independently selected from: a single bond, 1,4-cyclohexylene, and 1,4-phenylene, wherein hydrogen in 1,4-phenylene may each be independently substituted with one or more halogens; and the halogen is fluorine, chlorine, bromine or iodine; and $Z_1$ and $Z_2$ are both single bonds.

3. The liquid crystal compound according to claim 1, wherein the compound is characterized in that R is selected from H and unsubstituted alkyl containing 1-5 carbon atoms;

$A_1$ is selected from a single bond, 1,4-cyclohexylene and 1,4-phenylene, wherein hydrogen in 1,4-phenylene may be each independently substituted with one or more halogens; the halogen is fluorine, chlorine, bromine or iodine;

$A_2$ and $A_3$ are each independently selected from 1,4-cyclohexylene and 1,4-phenylene, wherein hydrogen in 1,4-phenylene may be each independently substituted with one or more halogens; the halogen is fluorine, chlorine, bromine or iodine; and $Z_1$ and $Z_2$ are both single bonds.

4. The liquid crystal compound according to claim 3, wherein the compound is characterized in that the halogen is fluorine.

5. The liquid crystal compound according to claim 1, wherein the liquid crystal compound is selected from liquid crystal compounds having structures represented by the following general formulas:

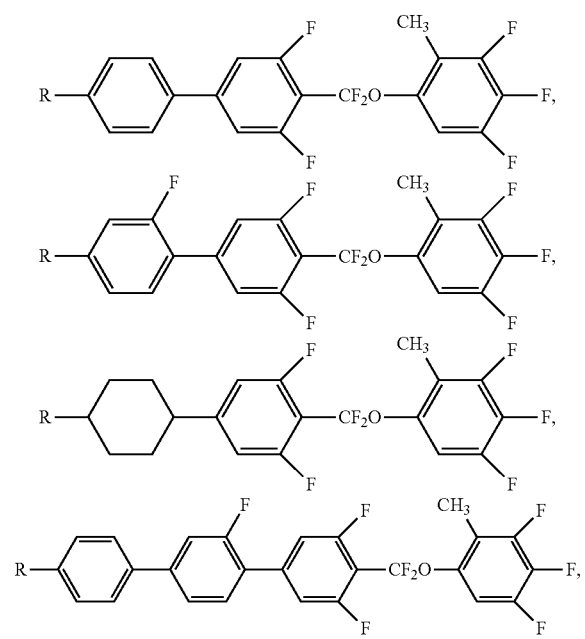

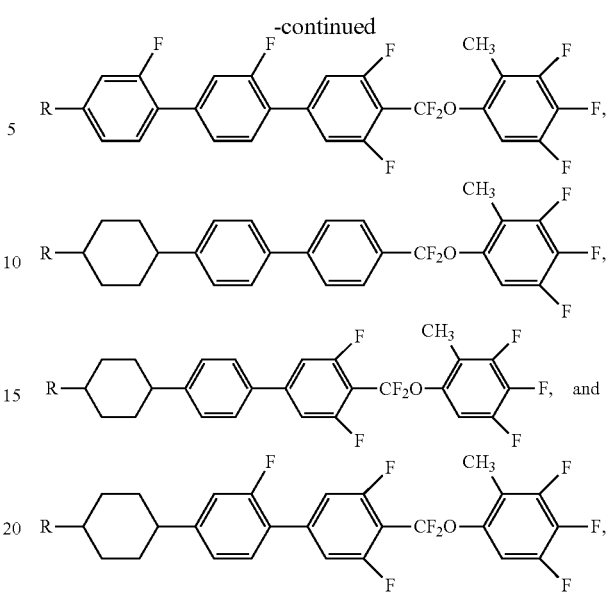

wherein R is selected from alkyl having 1-5 carbon atoms.

6. The liquid crystal compound according to claim 5, wherein the liquid crystal compound is:

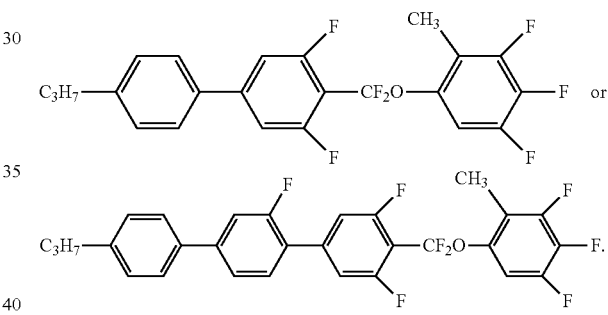

7. A liquid crystal composition containing the liquid crystal compound according to claim 1.

8. The liquid crystal composition according to claim 7, wherein the percentage of the liquid crystal compound is in the range of 1-80%.

9. A liquid crystal display comprising the liquid crystal compound according to claim 1.

10. A liquid crystal display comprising the liquid crystal composition according to claim 7.

11. A liquid crystal display comprising the liquid crystal composition according to claim 8.

12. The liquid crystal composition according to claim 7, wherein the percentage of the liquid crystal compound is in the range of 3-50%.

13. A liquid crystal display comprising the liquid crystal composition according to claim 12.

14. The liquid crystal compound according to claim 2, wherein the halogen is fluorine.

15. The liquid crystal compound according to claim 3, wherein the halogen is fluorine.

* * * * *